(12) United States Patent
Miyamoto

(10) Patent No.: US 8,077,217 B2
(45) Date of Patent: Dec. 13, 2011

(54) EYEBALL PARAMETER ESTIMATING DEVICE AND METHOD

(75) Inventor: Shinichi Miyamoto, Tokyo (JP)

(73) Assignee: NEC Corporation, Tokyo (JP)

( * ) Notice: Subject to any disclaimer, the term of this patent is extended or adjusted under 35 U.S.C. 154(b) by 375 days.

(21) Appl. No.: 12/517,529

(22) PCT Filed: Nov. 27, 2007

(86) PCT No.: PCT/JP2007/073273
§ 371 (c)(1),
(2), (4) Date: Jun. 3, 2009

(87) PCT Pub. No.: WO2008/069158
PCT Pub. Date: Jun. 12, 2008

(65) Prior Publication Data
US 2010/0013949 A1 Jan. 21, 2010

(30) Foreign Application Priority Data
Dec. 5, 2006 (JP) .................. 2006-328548

(51) Int. Cl.
*H04N 5/228* (2006.01)
(52) U.S. Cl. .................. 348/222.1
(58) Field of Classification Search ............ 348/222.1
See application file for complete search history.

(56) References Cited

U.S. PATENT DOCUMENTS

| | | | | |
|---|---|---|---|---|
| 5,016,282 A | * | 5/1991 | Tomono et al. | 382/117 |
| 5,818,954 A | * | 10/1998 | Tomono et al. | 382/115 |
| 7,834,912 B2 | * | 11/2010 | Yoshinaga et al. | 348/222.1 |
| 2003/0123027 A1 | * | 7/2003 | Amir et al. | 351/209 |
| 2006/0227103 A1 | * | 10/2006 | Koo et al. | 345/156 |

FOREIGN PATENT DOCUMENTS

| | | |
|---|---|---|
| JP | 1990224637 A | 9/1990 |
| JP | 1995055941 A | 3/1995 |
| JP | 2003015816 A | 1/2003 |
| JP | 2005230049 A | 9/2005 |
| WO | 0209025 A | 1/2002 |

OTHER PUBLICATIONS

International Search Report for PCT/JP2007/073273 mailed Mar. 18, 2008.

* cited by examiner

*Primary Examiner* — James Hannett

(57) ABSTRACT

A head posture estimating unit estimates, from a face image of a person photographed by a camera, a head posture of the person in a camera coordinate system. A head coordinate system eyeball central position candidate setting unit sets candidates of an eyeball central position in a head coordinate system based on two-point eyeball feature coordinates expressed in the head coordinate system. A camera coordinate system eyeball central position calculating unit calculates an eyeball central position ($\vec{a}$) in the camera coordinate system based on the head posture resulting from the estimating of the head posture estimating unit, the candidates of the eyeball central position set by the head coordinate system eyeball central position candidate setting unit, and a pupil central position detected from the face image. An eyeball parameter estimating unit estimates an eyeball central position (O) and an eyeball radius (r) in the head coordinate system based on the eyeball central position ($\vec{a}$) in the camera coordinate system.

23 Claims, 3 Drawing Sheets

EYEBALL PARAMETER ESTIMATING DEVICE AND METHOD

This application is the National Phase of PCT/JP2007/073273, filed Nov. 27, 2007, which is based upon and claims the benefit of priority from Japanese Patent Application No. 2006-328548, filed on Dec. 5, 2006, the disclosure of which is incorporated in its entirety by reference.

TECHNICAL FIELD

This invention relates to an eyeball parameter estimating device and method, and more particularly, to an eyeball parameter estimating device and method for estimating, from a camera image, as eyeball parameters, an eyeball central position and an eyeball radius which are required to estimate a line of sight of a person in the camera image.

BACKGROUND ART

Technologies of recognizing and predicting feelings and behaviors of humans using machines are widely needed for society. For example, in order to realize robots more friendly with humans, it is necessary to recognize the feeling of other person. When whether or not a person behaves suspiciously can be determined from behavior prediction based on camera images from a monitoring camera, the number of staffs performing monitoring tasks can be reduced to save effort. An example of a key important to recognize the feelings of humans and to predict the behaviors thereof includes the line of sight of a person. This is because, though humans think or determine behaviors based on information obtained from external fields, most of the information is visual information.

For example, it is assumed that a camera is pointed at a driver of a vehicle and the line of sight of the driver is estimated from a camera image obtained using the pointed camera. In such a situation, it is assumed that it is found from the estimated line of sight of the driver that the driver intends to turn the vehicle to the left without seeing a motorcycle approaching from the left side of the vehicle. In this case, a behavior such as involved driving can be predicted. In addition, it is assumed that a camera is pointed at a viewer of a commercial display and the line of sight of the person standing in front of the display is estimated from a camera image obtained using the pointed camera. In such a situation, it is assumed that it is found from the estimated line of sight of the person that the point of gaze thereof is focused. In this case, it is possible to obtain information that the viewer shows an interest in information displayed at a position of the point of gaze.

The line of sight is a straight line in a three-dimensional space. Therefore, in order to define the line of sight, it is necessary to set two points in the three-dimensional space. Various methods involving defining the line of sight are expected. A first method is based on the idea that an eyeball is assumed as a structure in which a sphere forming a crystalline lens and a partial sphere forming a cornea portion are combined and a center of the cornea partial sphere and a center of a pupil are assumed as two points for defining the line of sight. The first method is normally called a "corneal reflection method" and disclosed in, for example, JP 07-055941 A (hereinafter referred to as "Patent Document 1"). According to the corneal reflection method, a rotation angle of the eyeball in a coordinate system fixed to a head is calculated based on a reflection light image (cornea reflection image or Purkinje image) observed in an eye region when the eyeball is irradiated with near-infrared illumination light, the center of the pupil, and an illumination relative position. A representation of a head posture in a world coordinate system which is estimated using any method and an eyeball rotation are combined to estimate the line of sight in the world coordinate system. Note that the "world coordinate system" means a coordinate system arbitrarily determined without depending on both a person and a camera.

Hereinafter, a three-dimensional coordinate system determined in association with a camera photographing a person is referred to as a "camera coordinate system", and a coordinate system determined in association with the head of the person is referred to as a "head coordinate system". The eyeball can reflect light from various light sources, and hence it is normally difficult to obtain a correspondence between an illumination light source and the cornea reflection image. Therefore, the corneal reflection method is effective in a case where the camera photographing the eye region and the illumination light source are significantly close to the person (for example, camera and illumination light source are incorporated in head mount display). However, the corneal reflection method has a problem that the person is required to wear the camera or the like and thus has inconvenience.

On the other hand, the second method is based on the idea that the eyeball is assumed as a single sphere and the center of the eyeball and the center of the pupil are assumed as two points for defining the line of sight. According to this idea (second method), the line of sight can be estimated without depending on positions of the camera and the illumination light source with respect to the person. Hereinafter, a combination of an eyeball central position and an eyeball radius is referred to as eyeball parameters.

The pupil is a feature point appearing on a surface of the eyeball, and hence a pupil central position can be detected from the camera image. However, the center of the eyeball is positioned in an inner portion of a human, and hence the eyeball central position cannot be directly detected from the camera image.

Various related technologies of estimating the eyeball central position have been known.

According to a face image processing system described in, for example, JP 2004-504684 A (WO 02/009025 A1) (hereinafter referred to as "Patent Document 2"), during a calibration operation for estimating the eyeball central position, a person to be examined gazes on the point of gaze with known coordinates in a plurality of postures. The eyeball central position is estimated based on the fact that the line of sight passes through the set point of gaze in each of the postures.

In a system described in JP 2003-015816 A (hereinafter referred to as "Patent Document 3"), it is assumed that the center of the eyeball is positioned on a straight line which passes through a middle point between the inner corner of the eye and the outer corner of the eye and has a directional vector determined from a head posture.

DISCLOSURE OF THE INVENTION

Problem to be Solved by the Invention

A problem of the related technologies is that it is impossible to realize the estimation of the eyeball central position, in which calculation is stably converged at high speed while an eyeball radius varying between individuals is taken into account.

Patent Document 2 describes that the eyeball central position is estimated based on a head posture and a geometrical property and position of the eyeball. However, there is no specific description thereof.

Patent Document 3 has no specific description of the directional vector determined from the head posture. Even when the directional vector is determined, the eyeball central position cannot be determined unless the eyeball radius is known. Patent Document 3 does not describe a method for how to estimate the eyeball radius essentially varying between individuals.

In view of the above, an exemplary object of this invention is to provide, in the following manner, an eyeball parameter estimating device and method for stably estimating the eyeball central position and eyeball radius of a person at high speed. The person gazes the point of gaze which is specified in advance. The eyeball is assumed as a perfect sphere. The eyeball radius is set as one of parameters to be estimated. A positional relationship between two feature points located on the eyeball is used under the above-mentioned conditions.

Means to Solve the Problem

An eyeball parameter estimating device according to a first aspect of this invention includes: a head posture estimating unit for estimating, from a face image of a person photographed by a camera, position data corresponding to three degrees of freedom (x-, y-, z-axes) in a camera coordinate system, of an origin in a head coordinate system and rotation angle data corresponding to three degrees of freedom (x-, y-, z-axes) of a coordinate axis of the head coordinate system relative to a coordinate axis of the camera coordinate system, as head posture data in the camera coordinate system; a head coordinate system eyeball central position candidate setting unit for setting candidates of eyeball central position data in the head coordinate system based on coordinates of two feature points on an eyeball, which are preliminarily set in the head coordinate system; a camera coordinate system eyeball central position calculating unit for calculating an eyeball central position in the camera coordinate system based on the head posture data, the eyeball central position candidate data, and pupil central position data detected from the face image; and an eyeball parameter estimating unit for estimating an eyeball central position and an eyeball radius based on the eyeball central position in the camera coordinate system so as to minimize deviations of position data of a point of gaze, a pupil center, and an eyeball center from a straight line joining original positions of the three pieces of position data.

An eyeball parameter estimating method according to a second aspect of this invention includes: a first step of estimating, from a face image of a person photographed by a camera, position data corresponding to three degrees of freedom (x-, y-, z-axes) in a camera coordinate system, of an origin in a head coordinate system and rotation angle data corresponding to three degrees of freedom (x-, y-, z-axes) of a coordinate axis of the head coordinate system relative to a coordinate axis of the camera coordinate system, as head posture data in the camera coordinate system; a second step of setting candidates of eyeball central position data in the head coordinate system based on coordinates of two feature points on an eyeball, which are preliminarily set in the head coordinate system; a third step of calculating an eyeball central position in the camera coordinate system based on the estimated head posture data, the set eyeball central position candidate data, and pupil central position data detected from the face image; and a fourth step of estimating an eyeball central position and an eyeball radius based on the eyeball central position in the camera coordinate system so as to minimize deviations of position data of a point of gaze, a pupil center, and an eyeball center from a straight line joining original positions of the three pieces of position data.

EFFECT OF THE INVENTION

According to this invention, an existence area of the eyeball central position is limited based on the feature points located on the eyeball, and the eyeball central position in the head coordinate system and the eyeball central position in the camera coordinate system are combined. Therefore, the eyeball central position can be stably estimated at high speed. In addition, the eyeball radius is set as one of the eyeball parameters to be estimated, whereby the eyeball central position can be estimated with high precision while an individual difference of the eyeball radius is taken into account.

BEST MODE FOR EMBODYING THE INVENTION

Hereinafter, an embodiment of this invention is described in detail with reference to the attached drawings.

Figure 1:
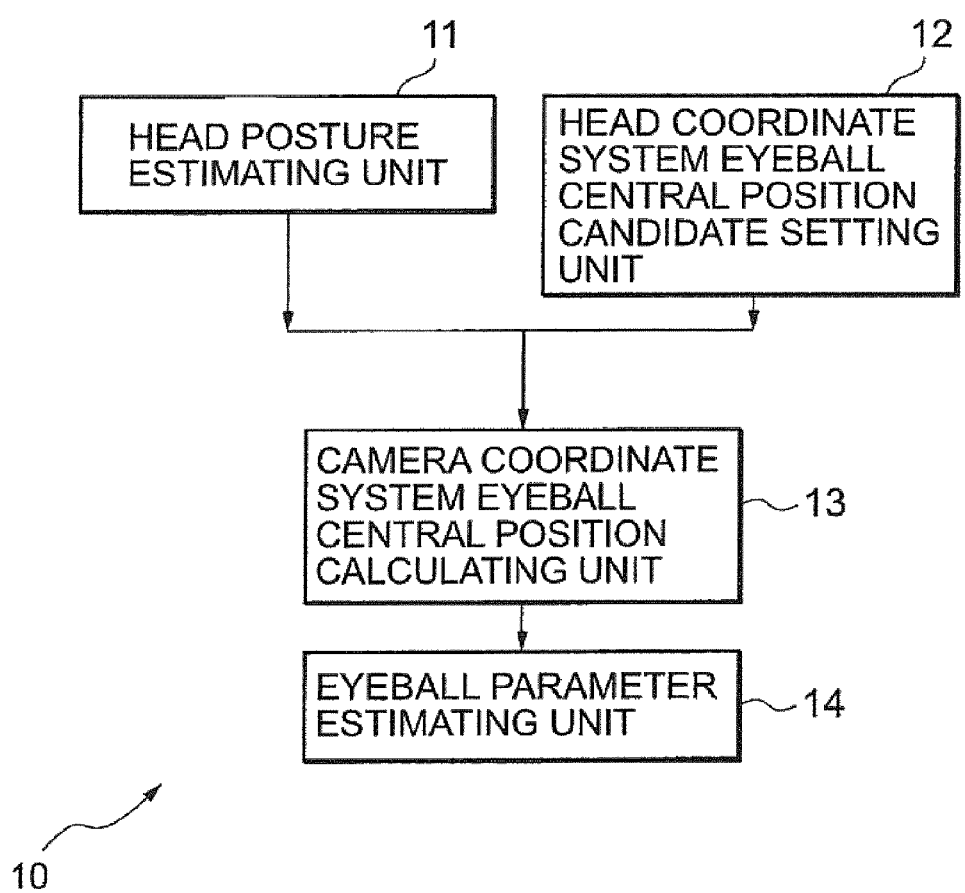
FIG. 1 is a block diagram illustrating a structure of an eyeball parameter estimating device according to an embodiment of this invention.

Referring to FIG. 1, an eyeball parameter estimating device 10 according to the embodiment of this invention includes a head posture estimating unit 11, a head coordinate system eyeball central position candidate setting unit 12, a camera coordinate system eyeball central position calculating unit 13, and an eyeball parameter estimating unit 14.

The head posture estimating unit 11 estimates, from a face image of a person photographed by an in-vehicle photographing camera, a head posture of the person. The head coordinate system eyeball central position candidate setting unit 12 sets candidates of an eyeball central position in a head coordinate system based on two eyeball feature point coordinates represented by the head coordinate system. The camera coordinate system eyeball central position calculating unit 13 calculates an eyeball central position in a camera coordinate system based on the head posture which is the result obtained by estimation by the head posture estimating unit 11, the candidates of the eyeball central position set by the head coordinate system eyeball central position candidate setting unit 12, and a pupil central position detected from the face image. The eyeball parameter estimating unit 14 estimates an eyeball central position and an eyeball radius in the head coordinate system based on the eyeball central position in the camera coordinate system which is set by the camera coordinate system eyeball central position calculating unit 13.

Next, an entire operation of the eyeball parameter estimating device 10 according to this embodiment is described with reference to the attached drawings. As illustrated in FIG. 1, the eyeball parameter estimating device 10 according to the embodiment of this invention comprises the head posture estimating unit 11, the head coordinate system eyeball central position candidate setting unit 12, the camera coordinate system eyeball central position calculating unit 13, and the eyeball parameter estimating unit 14.

Firstly, by reconstructing a three-dimensional shape of the head using a stereo camera, the head posture estimating unit 11 calculates a position and direction of the head in a three-dimensional space and adjusts the position and direction of the three-dimensional face model in the three-dimensional space so as to minimize an error with an input face image.

Alternatively, by attaching a texture in which an illumination condition is taken into account to a surface of a three-dimensional head model prepared in advance, to reproduce the appearance of the face image, the head posture estimating unit 11 adjusts the position and direction of the three-dimensional face model in the three-dimensional space so as to minimize the error with the input face image. Next, the head posture estimating unit 11 estimates, as head posture data, position data (three degrees of freedom) in the camera coordinate system, of an origin O' in a head coordinate system (FIG. 4) and rotation angle data (three degrees of freedom) of a coordinate axis of the head coordinate system with respect to a coordinate axis of the camera coordinate system, six degrees of freedom in total.

The head coordinate system eyeball central position candidate setting unit 12 reads coordinates of two feature points (for example, inner corner of eye and outer corner of eye) on an eyeball in the head coordinate system which are preliminarily prepared and an eyeball radius r which is provisionally determined. Then, the head coordinate system eyeball central position candidate setting unit 12 produces spheres whose radii are r and centers are the two feature points, and sets candidates of an eyeball central position in the head coordinate system on a cross circle of the two spheres.

The camera coordinate system eyeball central position calculating unit 13 represents the candidates of the eyeball central position in the head coordinate system by the camera coordinate system using the head posture data. Then, the camera coordinate system eyeball central position calculating unit 13 detects, from an image, a pupil center i (FIG. 4) of a person gazing on a specified point of gaze O" (FIG. 4), and calculates an eyeball central position $\vec{a}$ (FIG. 4) in the camera coordinate system so that a positional relationship among the point of gaze O", the pupil center i, and an eyeball center O (FIG. 4) becomes close to the same straight line.

The eyeball parameter estimating unit 14 learns (estimates) the eyeball central position O and the eyeball radius r in the head coordinate system based on the eyeball central position $\vec{a}$ in the camera coordinate system so as to minimize a deviation of the positional relationship among the point of gaze O", the pupil center i, and the eyeball center O from the straight line.

In order to detect the pupil center, any image processing for detecting a circular black region, such as template matching or Hough transform, may be used.

In the head posture estimating unit 11 in the first embodiment described above, the head posture estimating method based on the stereo camera method and the face appearance model has been described. As long as it is unnecessary to attach a measurement device to a human body, any posture estimating method may be used.

When the eyeball radius is assumed to be a fixed value in the first embodiment, only the eyeball central position may be estimated as the eyeball parameter.

The eyeball parameter estimating device 10 can be realized by a program executed by a computer.

Hereinafter, the operation of the entire eyeball parameter estimating device 10 according to the embodiment of this invention is described in detail with reference to FIGS. 1 and 2. Note that a case where the point of gaze is assumed to be the lens center O" of the camera for obtaining the face image is described below. However, as long as the position of the point of gaze in the camera coordinate system is already known, the eyeball central position and the eyeball radius can be estimated by the same processing method as described below based on the fact that the eyeball center, the pupil center, and the point of gaze are located on the straight line.

Figure 2:
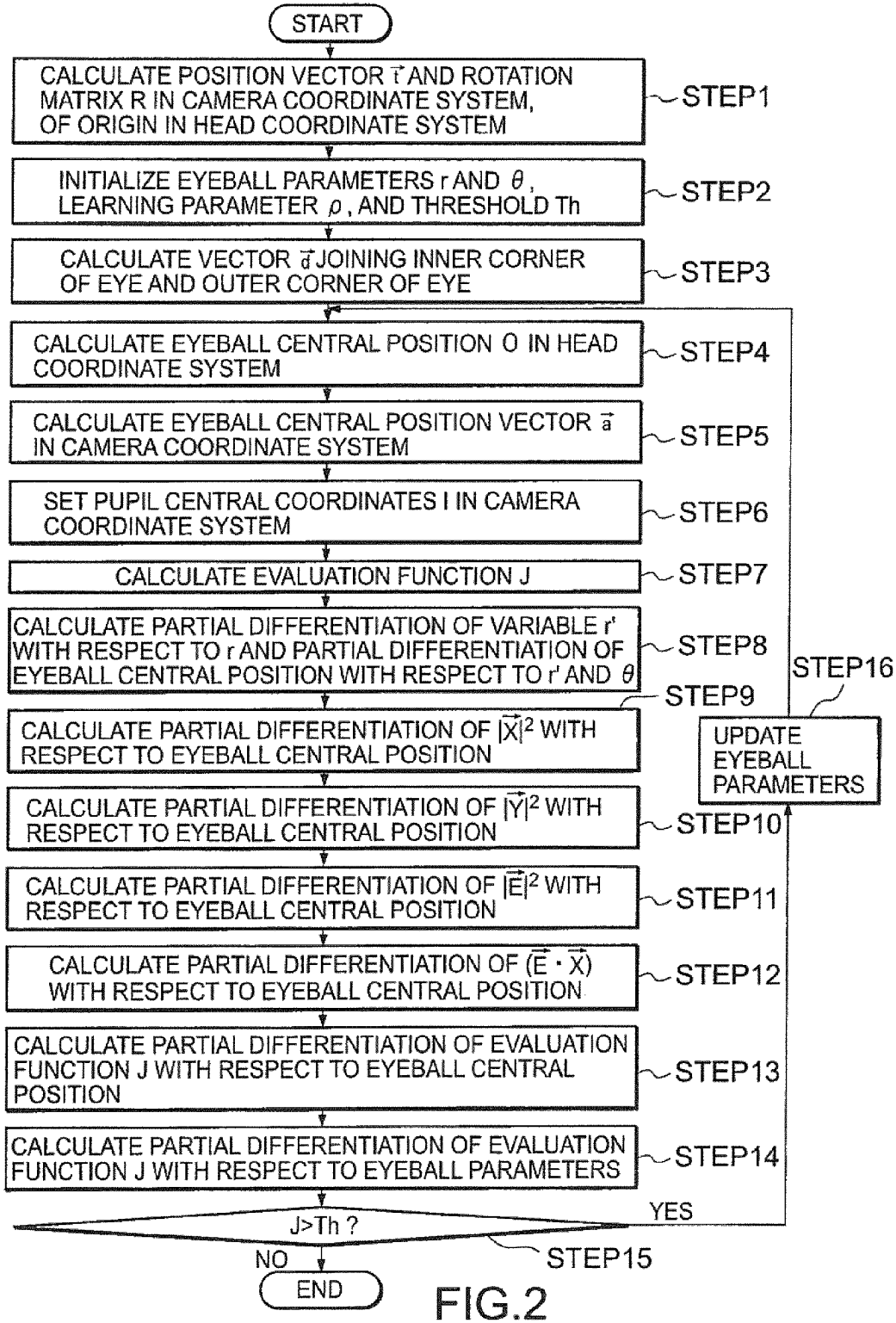
FIG. 2 is a flowchart illustrating an eyeball parameter estimating method according to the embodiment of this invention.

FIG. 2 is a flowchart illustrating processing of the eyeball parameter estimating device 10. STEP 1 illustrates the operation of the head posture estimating unit 11. STEP 3 and STEP 4 show the operation of the head coordinate system eyeball central position candidate setting unit 12. STEP 5 and STEP 6 show the operation of the camera coordinate system eyeball central position calculating unit 13. STEP 2 and STEP 7 to STEP 16 show the operation of the eyeball parameter estimating unit 14.

In STEP 1, the head posture estimating unit 11 calculates, based on the face image, a position vector $\vec{t}$ (FIG. 4) in the camera coordinate system, of the origin O' in the head coordinate system (FIG. 4) of the person and a rotation matrix R in a case where rotation angles of a coordinate axis of the head coordinate system relative to x-, y-, and z-axes of the camera coordinate system are expressed by α, β, and γ.

The above-mentioned position vector $\vec{t}$ is expressed by the following expression (1).

$$\vec{t} = (t_x, t_y, t_z) \tag{1}$$

The above-mentioned rotation matrix R is expressed by the following expression (2).

$$R = \begin{bmatrix} R_{00} & R_{01} & R_{02} \\ R_{10} & R_{11} & R_{12} \\ R_{20} & R_{21} & R_{22} \end{bmatrix} \tag{2}$$

$$= \begin{bmatrix} \cos\beta\cos\gamma & \begin{array}{l}-\cos\alpha\cos\gamma + \\ \sin\alpha\sin\beta\cos\gamma\end{array} & \begin{array}{l}\sin\alpha\sin\gamma + \\ \cos\alpha\sin\beta\cos\gamma\end{array} \\ \cos\beta\sin\gamma & \begin{array}{l}\cos\alpha\cos\gamma + \\ \sin\alpha\sin\beta\sin\gamma\end{array} & \begin{array}{l}-\sin\alpha\cos\gamma + \\ \cos\alpha\sin\beta\sin\gamma\end{array} \\ -\sin\beta & \sin\alpha\cos\beta & \cos\alpha\sin\beta \end{bmatrix}$$

In STEP 2, the eyeball parameter estimating unit 14 initializes the eyeball radius r, a phase angle θ indicative of the position of the eyeball center in the eyeball, a learning coefficient ρ, and a threshold Th used to determine the completion of learning. Note that the phase angle θ is described in STEP 4.

In STEP 3, the head coordinate system eyeball central position candidate setting unit 12 calculates a unit vector $\vec{d}$ joining the inner corner of the eye and the outer corner of the eye. The unit vector $\vec{d}$ is expressed by the following expression (3). Note that a superscript t indicates a transpose vector.

$$d = (l, m, n)^t \tag{3}$$

In STEP 4, the head coordinate system eyeball central position candidate setting unit 12 calculates trigonometric functions in accordance with the following expressions (4), (5), (6), and (7) based on the elements of the unit vector $\vec{d}$ determined in STEP 3.

$$\sin A' = -m \tag{4}$$

$$\sin B' = \frac{1}{\sqrt{1-m^2}} \tag{5}$$

$$\cos A' = \sqrt{1-m^2} \tag{6}$$

$$\cos B' = \frac{\sqrt{1-m^2-l^2}}{\sqrt{1-m^2}} \tag{7}$$

By using those values, the head coordinate system eyeball central position candidate setting unit 12 calculates a rotation matrix R' expressed by the following expression (8).

$$R' = \begin{bmatrix} R'_{00} & R'_{01} & R'_{02} \\ R'_{10} & R'_{11} & R'_{12} \\ R'_{20} & R'_{21} & R'_{22} \end{bmatrix} \quad (8)$$

$$= \begin{bmatrix} \cos B' & \sin A' \sin B' & \cos A' \sin B' \\ 0 & \cos A' & -\sin A' \\ -\sin B' & \sin A' \cos B' & \cos A' \cos B' \end{bmatrix}$$

Figure 3:
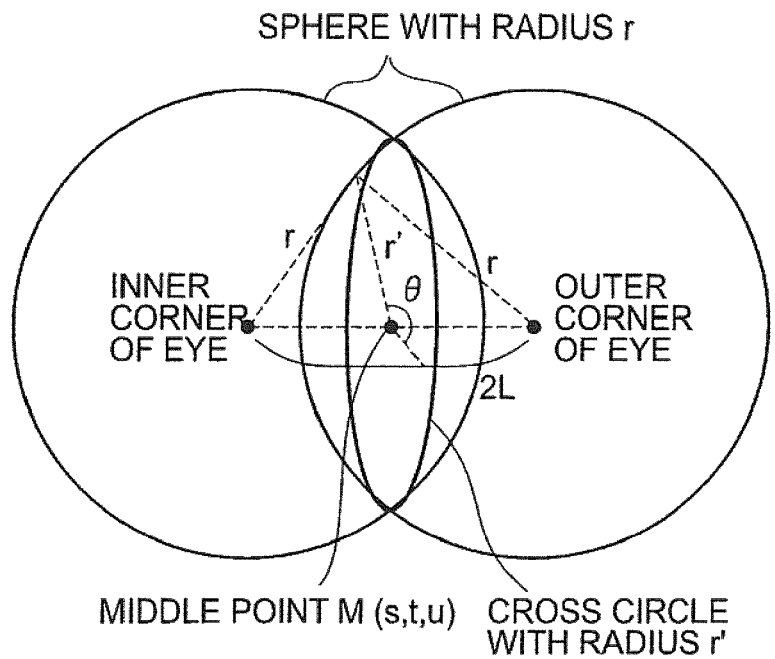
FIG. 3 illustrates a method of setting an eyeball central position in a head coordinate system.

As illustrated in FIG. 3, it is assumed that a distance between the inner corner and outer corner of the eye is expressed by 2 L. In this case, a cross circle of spheres with the radius r at the inner corner and outer corner of the eye as centers is a circle with a radius r' at a middle point M=(s, t, u) between the inner corner and outer corner of the eye as center. The eyeball center is located on a circumference of the circle. In this case, the radius r' is expressed by the following expression (9).

$$r' = \sqrt{r^2 - L^2} \quad (9)$$

In STEP 4, the camera coordinate system eyeball central position calculating unit 13 sets candidates of an eyeball central position O=(Ox, Oy, Oz) in the head coordinate system so as to satisfy a relationship of the following expression (10) in a case where a phase angle when the circle is expressed with polar coordinates is expressed by θ.

$$\begin{bmatrix} O_x \\ O_y \\ O_z \end{bmatrix} = \begin{bmatrix} s \\ t \\ u \end{bmatrix} + R' \begin{bmatrix} r' \cos\theta \\ r' \sin\theta \\ 0 \end{bmatrix} \quad (10)$$

In STEP 5, the camera coordinate system eyeball central position calculating unit 13 calculates an eyeball central position vector $\vec{a}$ in the camera coordinate system using a relational expression of the following expression (11) based on the position vector $\vec{t}$ in the camera coordinate system, of the origin in the head coordinate system and the rotation matrix R which are calculated in STEP 1 in a case where the eyeball central position in the head coordinate system which is set in STEP 4 is expressed by $\vec{a}'$.

$$\vec{a} = \vec{t} + R\vec{a}' \quad (11)$$

Note that the eyeball central position vector $\vec{a}$ is expressed by the following expression (12).

$$\vec{a} = (a_x, a_y, a_z) \quad (12)$$

In a perspective transformation camera model, when pupil central coordinates on an image are expressed by (I'x, I'y), I'x and I'y are expressed by the following expressions (13) and (14), respectively.

$$I'x = \frac{Ix}{Iz}f + v \quad (13)$$

$$I'y = \frac{Iy}{Iz}f + w \quad (14)$$

When image central coordinates are expressed by (v, w) and a focal distance is expressed by f, pupil central coordinates (Ix, Iy, Iz) in the camera coordinate system are expressed by the following expressions (15) and (16).

$$Ix = \frac{I'x - v}{f}Iz = kxIz \quad (15)$$

$$Iy = \frac{I'y - w}{f}Iz = kyIz \quad (16)$$

Figure 4:
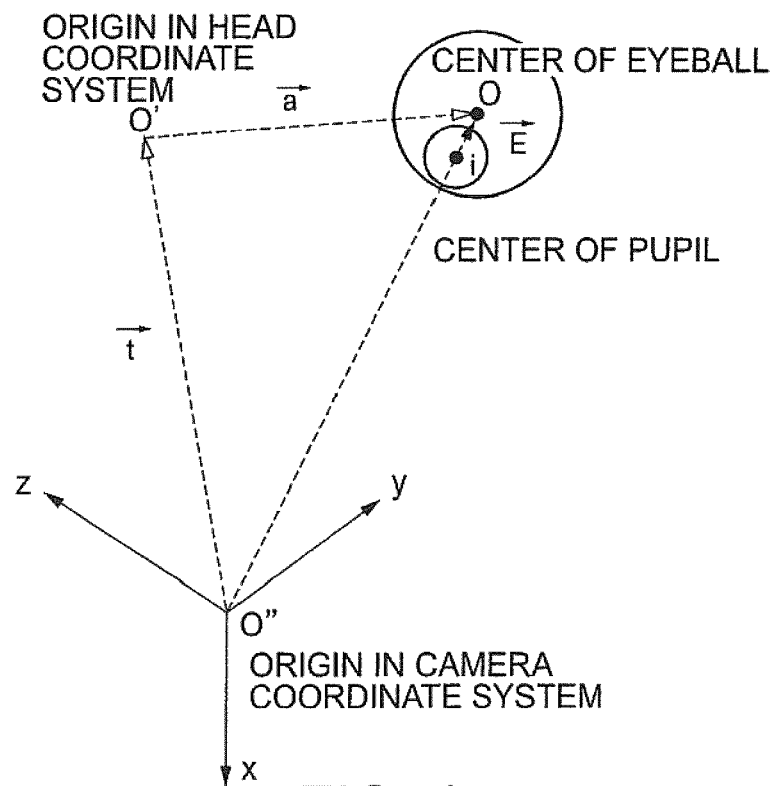
FIG. 4 illustrates a positional relationship among a center of an eyeball, a center of a pupil, and a lens center of a camera.

In FIG. 4, a distance X between the origin O" in the camera coordinate system and the eyeball center can be obtained by the following expression (17).

$$X = |\vec{X}| = |\vec{t} + \vec{a}| \quad (17)$$

In such a case, the following expressions (18) and (19) are derived.

$$Ix^2 + Iy^2 + Iz^2 = (X - r)^2 \quad (18)$$

$$Iz = \frac{X - r}{\sqrt{1 + kx^2 + ky^2}} = \frac{K_1}{k_2} \quad (19)$$

In STEP 6, the camera coordinate system eyeball central position calculating unit 13 sets the pupil central coordinates in the camera coordinate system by the following expression (20) using the above-mentioned expressions (15), (16), and (19).

$$\begin{bmatrix} Ix \\ Iy \\ Iz \end{bmatrix} = \frac{k_1}{k_2} \begin{bmatrix} kx \\ ky \\ 1 \end{bmatrix} \quad (20)$$

From FIG. 4, it is assumed that a vector pointing from the pupil center i to the eyeball center O in the camera coordinate system is expressed by $\vec{E}$.

In this case, the eyeball center O, the pupil center i, and the origin O" in the camera coordinate system are located on the straight line. Therefore, the vector $\vec{E}$ pointing from the pupil center i to the eyeball center O can be determined by the following expression (21).

$$\vec{E} = \frac{|\vec{O} - \vec{i}|}{|\vec{t} + \vec{a}|}(\vec{t} + \vec{a}) \quad (21)$$

$$= \frac{r}{X}(\vec{t} + \vec{a})$$

An absolute value Y of a difference $\vec{Y}$ between a position vector $\vec{O}$ of the eyeball center and a position vector $\vec{i}$ of the pupil center is expressed by the following expression (22).

$$Y = |\vec{Y}| = |\vec{O} - \vec{i}| \quad (22)$$

Then, in STEP 7, the eyeball parameter estimating unit 14 calculates an evaluation function J using the following expression (23).

$$J = |X\vec{E} - Y\vec{X}| \quad (23)$$

A value of the evaluation function is originally zero, but the value does not become zero in a strict sense because of estimation error of the eyeball parameter or detection error of the pupil center. Therefore, in STEP 8 to STEP 16, the eyeball parameter estimating unit 14 learns (estimates) the eyeball parameter r and the phase angle θ so as to minimize the evaluation function J expressed by the expression (23).

In STEP 8, the eyeball parameter estimating unit 14 calculates the partial differentiation of a variable r' with respect to the eyeball radius r and the partial differentiation of the eyeball central coordinates O in the head coordinate system with respect to the parameters r' and θ, using the following expressions (24) to (30).

$$\frac{\partial r'}{\partial r} = \frac{r}{\sqrt{r^2 - L^2}} \quad (24)$$

$$\frac{\partial O_x}{\partial r} = R'_{00}\cos\theta + R'_{01}\sin\theta \quad (25)$$

$$\frac{\partial O_y}{\partial r} = R'_{10}\cos\theta + R'_{11}\sin\theta \quad (26)$$

$$\frac{\partial O_z}{\partial r} = R'_{20}\cos\theta + R'_{21}\sin\theta \quad (27)$$

$$\frac{\partial O_x}{\partial \theta} = r'(-R'_{00}\sin\theta + R'_{01}\cos\theta) \quad (28)$$

$$\frac{\partial O_y}{\partial \theta} = r'(-R'_{10}\sin\theta + R'_{11}\cos\theta) \quad (29)$$

$$\frac{\partial O_z}{\partial \theta} = r'(-R'_{20}\sin\theta + R'_{21}\cos\theta) \quad (30)$$

In STEP 9, the eyeball parameter estimating unit 14 calculates the partial differentiation of a square $|\vec{X}|^2$ of the distance X with respect to the eyeball central position O using the following expressions (31) to (33).

$$\frac{\partial |\vec{X}|^2}{\partial O_x} = 2\{(t_x + a_x)R_{00} + (t_y + a_y)R_{01} + (t_z + a_z)R_{02}\} = 2A \quad (31)$$

$$\frac{\partial |\vec{X}|^2}{\partial O_y} = 2\{(t_x + a_x)R_{01} + (t_y + a_y)R_{11} + (t_z + a_z)R_{21}\} = 2B \quad (32)$$

$$\frac{\partial |\vec{X}|^2}{\partial O_z} = 2\{(t_x + a_x)R_{02} + (t_y + a_y)R_{12} + (t_z + a_z)R_{22}\} = 2C \quad (33)$$

In STEP 10, the eyeball parameter estimating unit 14 calculates the partial differentiation of a square $|\vec{Y}|^2$ of the absolute value Y with respect to the eyeball central position O using the following expression (34).

$$\frac{\partial |\vec{Y}|^2}{\partial O_i} = 2(O_i - I_i)(i = x, y, z) \quad (34)$$

In STEP 11, the eyeball parameter estimating unit 14 calculates the partial differentiation of a square $|\vec{E}|^2$ of an absolute value of the vector $\vec{E}$ with respect to the eyeball central position O by the following expressions (35) to (37) using kx and ky in the above-mentioned expressions (15) and (16), $k_2$ in the above-mentioned expression (19), and A, B, and C in the above-mentioned expressions (31), (32), and (33).

$$\frac{\partial |\vec{E}|^2}{\partial O_x} = 2\left\{(t_x + a_x - I_x)\left(R_{00} - \frac{k_x A}{k_2 X} + \frac{k_x (\vec{Y})_x}{k_2 Y}\right)\right\} + \quad (35)$$
$$(t_y + a_x - I_x)\left(R_{10} - \frac{k_y A}{k_2 X} + \frac{k_y (\vec{Y})_x}{k_2 Y}\right) +$$
$$(t_z + a_z - I_z)\left(R_{20} - \frac{A}{k_2 X} + \frac{(\vec{Y})_x}{k_2 Y}\right)$$

$$\frac{\partial |\vec{E}|^2}{\partial O_y} = 2\left\{(t_x + a_x - I_x)\left(R_{01} - \frac{k_x B}{k_2 X} + \frac{k_x (\vec{Y})_y}{k_2 Y}\right)\right\} + \quad (36)$$
$$(t_y + a_y - I_y)\left(R_{11} - \frac{k_y B}{k_2 X} + \frac{k_y (\vec{Y})_y}{k_2 Y}\right) +$$
$$(t_z + a_z - I_z)\left(R_{21} - \frac{B}{k_2 X} + \frac{(\vec{Y})_y}{k_2 Y}\right)$$

$$\frac{\partial |\vec{E}|^2}{\partial O_z} = 2\left\{(t_x + a_x - I_x)\left(R_{02} - \frac{k_x C}{k_2 X} + \frac{k_x (\vec{Y})_z}{k_2 Y}\right)\right\} + \quad (37)$$
$$(t_y + a_y - I_y)\left(R_{12} - \frac{k_y C}{k_2 X} + \frac{k_y (\vec{Y})_z}{k_2 Y}\right) +$$
$$(t_z + a_z - I_z)\left(R_{22} - \frac{C}{k_2 X} + \frac{(\vec{Y})_z}{k_2 Y}\right)$$

Note that $(\vec{Y})_x$, $(\vec{Y})_y$, and $(\vec{Y})_z$ indicate x-, y-, and z-components of the difference $\vec{Y}$ respectively.

In STEP 12, the eyeball parameter estimating unit 14 calculates the partial differentiation of $\vec{E} \cdot \vec{X}$ with respect to the eyeball central position O by the following expressions (38) to (40) using kx and ky in the above-mentioned expressions (15) and (16), $k_2$ in the above-mentioned expression (19), and A, B, and C in the above-mentioned expressions (31), (32), and (33) in a case where $M = 1/k_2 X$ and $P = 1/k_2 Y$ are assumed.

$$\frac{\partial (\vec{E} \cdot \vec{X})}{\partial O_x} = [R_{00} - k_x\{MA - P(\vec{Y})_x\}](t_x + a_x) + \quad (38)$$
$$(t_x + a_x - I_x)R_{00} + [R_{10} - k_y\{MA - P(\vec{Y})_x\}](t_y + a_y) +$$
$$(t_y + a_y - I_y)R_{10} + [R_{20} - \{MA - P(\vec{Y})_x\}](t_z + a_z) +$$
$$(t_z + a_z - I_z)R_{20}$$

$$\frac{\partial (\vec{E} \cdot \vec{X})}{\partial O_y} = [R_{01} - k_x\{MB - P(\vec{Y})_y\}](t_x + a_x) + \quad (39)$$
$$(t_x + a_x - I_x)R_{01} + [R_{11} - k_y\{MB - P(\vec{Y})_y\}](t_y + a_y) +$$
$$(t_y + a_y - I_y)R_{11} + [R_{21} - \{MB - P(\vec{Y})_y\}](t_z + a_z) +$$
$$(t_z + a_z - I_z)R_{21}$$

$$\frac{\partial (\vec{E} \cdot \vec{X})}{\partial O_z} = [R_{02} - k_x\{MC - P(\vec{Y})_z\}](t_x + a_x) + \quad (40)$$
$$(t_x + a_x - I_x)R_{02} + [R_{12} - k_y\{MC - P(\vec{Y})_z\}](t_y + a_y) +$$
$$(t_y + a_y - I_y)R_{12} + [R_{22} - \{MC - P(\vec{Y})_z\}](t_z + a_z) +$$
$$(t_z + a_z - I_z)R_{22}$$

In STEP 13, the eyeball parameter estimating unit 14 calculates the partial differentiation of the evaluation function J with respect to the eyeball central position O based on the results obtained by the partial differentiation in STEP 9 to STEP 12. Specifically, the eyeball parameter estimating unit 14 calculates the partial differentiation of the evaluation function J with respect to the eyeball central position O using the following expression (41).

$$\frac{\partial J}{\partial O_i} = \frac{\partial |\vec{X}|^2}{\partial O_i}|\vec{E}|^2 + |\vec{X}|^2\frac{\partial |\vec{E}|^2}{\partial O_i} - \frac{|\vec{Y}|\partial |\vec{X}|^2}{|\vec{X}|\partial O_i}(\vec{E}\cdot\vec{X}) - \frac{|\vec{X}|\partial |\vec{Y}|^2}{|\vec{Y}|\partial O_i}(\vec{E}\cdot\vec{X}) - $$
$$2|\vec{X}||\vec{Y}|\frac{\partial(\vec{E}\cdot\vec{X})}{\partial O_i} + |\vec{X}|^2\frac{\partial |\vec{Y}|^2}{\partial O_i} + |\vec{Y}|^2\frac{\partial |\vec{X}|^2}{\partial O_i} \quad (i=x,y,z) \quad (41)$$

In STEP 14, the eyeball parameter estimating unit 14 calculates the partial differentiation of the evaluation function J with respect to the eyeball parameters r and θ using the above-mentioned expressions (25) to (30) which are the results in STEP 8, the above-mentioned expression (41) which is the result in STEP 13, and the following expressions (42) and (43).

$$\frac{\partial J}{\partial r} = \frac{\partial r'}{\partial r}\left(\frac{\partial O_x}{\partial r'}\frac{\partial J}{\partial O_x} + \frac{\partial O_y}{\partial r'}\frac{\partial J}{\partial O_y} + \frac{\partial O_z}{\partial r'}\frac{\partial J}{\partial O_z}\right) \quad (42)$$

$$\frac{\partial J}{\partial \theta} = \frac{\partial O_x}{\partial \theta}\frac{\partial J}{\partial O_x} + \frac{\partial O_y}{\partial \theta}\frac{\partial J}{\partial O_y} + \frac{\partial O_z}{\partial \theta}\frac{\partial J}{\partial O_z} \quad (43)$$

In STEP 15, the eyeball parameter estimating unit 14 compares the evaluation function J with the threshold Th. When J becomes smaller than Th, the eyeball parameter estimation processing is completed. When J is larger than Th, processing returns to STEP 4 and the eyeball parameter estimation processing continues.

In STEP 16, the eyeball parameter estimating unit 14 updates the eyeball parameters r and θ by the following expressions (44) and (45) using the expressions (42) and (43) which are the results in STEP 14.

$$r \leftarrow r + \rho\frac{\partial J}{\partial r} \quad (44)$$

$$\theta \leftarrow \theta + \rho\frac{\partial J}{\partial \theta} \quad (45)$$

According to this invention, the eyeball central position used to estimate the line of sight can be stably estimated at high speed, and the eyeball central position can be estimated with high precision while the individual difference of the eyeball radius is taken into account.

While the invention has been particularly shown and described with reference to the exemplary embodiment thereof, the invention is not limited to the embodiment described above. It will be understood by those of ordinary skill in the art that various changes in form and details may be therein without departing from the spirit and scope of the present invention as defined by the claims.

The invention claimed is:

1. An eyeball parameter estimating device, comprising:
a head posture estimating unit that estimates, from a face image of a person photographed by a camera, position data ($\vec{t}$) corresponding to three degrees of freedom (x-, y-, z-axes) in a camera coordinate system, of an origin (O') in a head coordinate system and rotation angle data (R) corresponding to three degrees of freedom (x-, y-, z-axes) of a coordinate axis of the head coordinate system relative to a coordinate axis of the camera coordinate system, as head posture data ($\vec{t}$, R) in the camera coordinate system;
a head coordinate system eyeball central position candidate setting unit that sets candidates of eyeball central position data ($\vec{a}'$) in the head coordinate system based on coordinates of two feature points on an eyeball, which are preliminarily set in the head coordinate system;
a camera coordinate system eyeball central position calculating unit that calculates an eyeball central position ($\vec{a}$) in the camera coordinate system based on the head posture data ($\vec{t}$, R), the eyeball central position candidate data ($\vec{a}'$), and pupil central position data detected from the face image; and
an eyeball parameter estimating unit that estimates an eyeball central position (O) and an eyeball radius (r) in the head coordinate system based on the eyeball central position ($\vec{a}$) in the camera coordinate system so as to minimize deviations of position data of a point of gaze (O''), a pupil center (i), and an eyeball center (O) from a straight line joining original positions of the three pieces of position data.

2. An eyeball parameter estimating device according to claim 1, wherein the two feature points on the eyeball which are used include an inner corner and an outer corner of an eye.

3. An eyeball parameter estimating device according to claim 2, wherein the point of gaze which is used includes a lens center (O'') of the camera for obtaining the face image.

4. An eyeball parameter estimating device according to claim 1, wherein:
the head posture estimating unit obtains, from the face image, the position data as a position vector $\vec{t}$ expressed by the following expression (1) in the camera coordinate system, of the origin (O') of the person in the head coordinate system:

$$\vec{t} = (t_x, t_y, t_z) \quad (1); \text{ and}$$

the head posture estimating unit obtains the rotation angle data as a rotation matrix R expressed by the following expression (2) when rotation angles of a coordinate axis of the head coordinate system relative to the x-, y-, and z-axes of the camera coordinate system are expressed by α, β, and γ:

$$R = \begin{bmatrix} R_{00} & R_{01} & R_{02} \\ R_{10} & R_{11} & R_{12} \\ R_{20} & R_{21} & R_{22} \end{bmatrix} = \quad (2)$$

$$\begin{bmatrix} \cos\beta\cos\gamma & -\cos\alpha\cos\gamma + \sin\alpha\sin\beta\cos\gamma & \sin\alpha\sin\gamma + \cos\alpha\sin\beta\cos\gamma \\ \cos\beta\sin\gamma & \cos\alpha\cos\gamma + \sin\alpha\sin\beta\sin\gamma & -\sin\alpha\cos\gamma + \cos\alpha\sin\beta\sin\gamma \\ -\sin\beta & \sin\alpha\cos\beta & \cos\alpha\sin\beta \end{bmatrix}.$$

5. An eyeball parameter estimating device according to claim 4, wherein the head coordinate system eyeball central position candidate setting unit reads the coordinates of the two feature points on the eyeball in the head coordinate system and the eyeball radius (r) which is provisionally determined, produces spheres having the eyeball radius (r) with the respective two feature points being as their centers, and sets candidates of an eyeball central position (O =(Ox, Oy, Oz)) in the head coordinate system on a cross circle of the two spheres.

6. An eyeball parameter estimating device according to claim 5, wherein the camera coordinate system eyeball central position calculating unit produces the eyeball central position candidate data in the head coordinate system by the camera coordinate system using the head posture data ($\vec{t}$, R), detects, from the face image, the pupil center (i) of the person gazing the point of gaze (O″), and calculates the eyeball central position ($\vec{a}$) in the camera coordinate system such that three positions of the point of gaze (O″), the pupil center (i), and the eyeball center (O) become close to each other on a same straight line.

7. An eyeball parameter estimating device according to claim 6, wherein the pupil center (i) is detected by image processing for detecting a circular black region of the face image.

8. An eyeball parameter estimating method, comprising:
a first step of estimating, from a face image of a person photographed by a camera, position data ($\vec{t}$) corresponding to three degrees of freedom (x-, y-, z-axes) in a camera coordinate system, of an origin (O') in a head coordinate system and rotation angle data (R) corresponding to three degrees of freedom (x-, y-, z-axes) of a coordinate axis of the head coordinate system relative to a coordinate axis of the camera coordinate system, as head posture data ($\vec{t}$, R) in the camera coordinate system;
a second step of setting candidates of an eyeball central position data ($\vec{a}'$) in the head coordinate system based on coordinates of two feature points on an eyeball, which are preliminarily set in the head coordinate system;
a third step of calculating an eyeball central position ($\vec{a}$) in the camera coordinate system based on the head posture data ($\vec{t}$, R), the eyeball central position candidate data ($\vec{a}'$), and pupil central position data detected from the face image; and a fourth step of estimating an eyeball central position (O) and an eyeball radius (r) in the head coordinate system based on the eyeball central position ($\vec{a}$) in the camera coordinate system so as to minimize deviations of position data of a point of gaze (O″), a pupil center (i), and an eyeball center (O) from a straight line joining original positions of the three pieces of position data.

9. An eyeball parameter estimating method according to claim 8, wherein the two feature points on the eyeball which are used include an inner corner and outer corner of an eye.

10. An eyeball parameter estimating method according to claim 9, wherein the point of gaze which is used includes a lens center (O″) of the camera for obtaining the face image.

11. An eyeball parameter estimating method according to claim 8, wherein, in the first step:
the position data is, from the face image, calculated as a position vector $\vec{t}$ expressed by the following expression (1) in the camera coordinate system, of the origin (O') of the person in the head coordinate system:

$$\vec{t} = (t_x, t_y, t_z) \qquad (1); \text{ and}$$

the rotation angle data is calculated as a rotation matrix R expressed by the following expression (2) when rotation angles of a coordinate axis of the head coordinate system relative to the x-, y-, and z-axes of the camera coordinate system are expressed by α, β, and γ:

$$R = \begin{bmatrix} R_{00} & R_{01} & R_{02} \\ R_{10} & R_{11} & R_{12} \\ R_{20} & R_{21} & R_{22} \end{bmatrix} = \qquad (2)$$

$$\begin{bmatrix} \cos\beta\cos\gamma & -\cos\alpha\cos\gamma + \sin\alpha\sin\beta\cos\gamma & \sin\alpha\sin\gamma + \cos\alpha\sin\beta\cos\gamma \\ \cos\beta\sin\gamma & \cos\alpha\cos\gamma + \sin\alpha\sin\beta\sin\gamma & -\sin\alpha\cos\gamma + \cos\alpha\sin\beta\sin\gamma \\ -\sin\beta & \sin\alpha\cos\beta & \cos\alpha\sin\beta \end{bmatrix}.$$

12. An eyeball parameter estimating method according to claim 11, wherein, in the second step:
the coordinates of the two feature points on the eyeball in the head coordinate system and the eyeball radius (r), which is provisionally determined, are read;
spheres having the eyeball radius (r) are produced with the respective two feature points being as their centers; and
candidates of an eyeball central position (O =(Ox, Oy, Oz)) in the head coordinate system are set on a cross circle of the two spheres.

13. An eyeball parameter estimating method according to claim 12, wherein, in the third step:
the eyeball central position candidate data in the head coordinate system is produced by the camera coordinate system using the head posture data ($\vec{t}$, R);
the pupil center (i) of the person gazing the point of gaze (O″) is detected from the face image; and
the eyeball central position ($\vec{a}$) in the camera coordinate system is calculated such that three positions of the point of gaze (O"), the pupil center (i), and the eyeball center (O) become close to each other on a same straight line.

14. An eyeball parameter estimating method according to claim 13, wherein the pupil center (i) is detected by image processing for detecting a circular black region of the face image.

15. An eyeball parameter estimating method according to claim 8, wherein:

in the fourth step the eyeball radius (r), a phase angle (θ) which indicates a position of the eyeball center in the eyeball and is expressed with polar coordinate, a learning coefficient (ρ), and a threshold (Th) used to determine a completion of learning are initialized;

in the second step, a unit vector $\vec{d}$ joining an inner corner and an outer corner of an eye, which is expressed by the following expression (3) using a superscript t as a transpose vector, is calculated:

$$\vec{d} = (l, m, n)^t \quad (3);$$

trigonometric functions are calculated in accordance with the following expressions (4), (5), (6), and (7) based on elements of the obtained unit vector $\vec{d}$: $\sin A' = -m;$ \quad (4)

$$\sin B' = \frac{1}{\sqrt{1-m^2}}; \quad (5)$$

$$\cos A' = \sqrt{1-m}; \text{ and} \quad (6)$$

$$\cos B' = \frac{\sqrt{1-m^2-l^2}}{\sqrt{1-m^2}}; \quad (7)$$

a rotation matrix R' expressed by the following expression (8) is calculated based on values of the trigonometric functions:

$$R' = \begin{bmatrix} R'_{00} & R'_{01} & R'_{02} \\ R'_{10} & R'_{11} & R'_{12} \\ R'_{20} & R'_{21} & R'_{22} \end{bmatrix} \quad (8)$$

$$= \begin{bmatrix} \cos B' & \sin A' \sin B' & \cos A' \sin B' \\ 0 & \cos A' & -\sin A' \\ -\sin B' & \sin A' \cos B' & \cos A' \cos B' \end{bmatrix};$$

when a distance between the inner corner and the outer corner of the eye is expressed by 2L, a cross circle of spheres having the radius (r) with the inner corner and the outer corner of the eye being as their centers is a circle having a radius (r') expressed by the following expression (9) with a middle point M=(s, t, u) between the inner corner and the outer corner of the eye being as their centers;

$$r' = \sqrt{r^2 - L^2} \quad (9); \text{ and}$$

when a phase angle in a case where the circle having the radius (r') is expressed with polar coordinate is expressed by θ, the candidates of the eyeball central position (O =(Ox, Oy, Oz)) in the head coordinate system are set so as to satisfy a relationship of the following expression (10):

$$\begin{bmatrix} O_x \\ O_y \\ O_z \end{bmatrix} = \begin{bmatrix} s \\ t \\ u \end{bmatrix} + R' \begin{bmatrix} r' \cos\theta \\ r' \cos\theta \\ 0 \end{bmatrix}. \quad (10)$$

16. An eyeball parameter estimating method according to claim 15, wherein, in the third step:

when the set eyeball central position is expressed by $\vec{a}'$, a relational expression of the following expression (11) is used:

$$\vec{a} = \vec{t} + R\vec{a}' \quad (11); \text{ and}$$

an eyeball central position vector $\vec{a}$ in the camera coordinate system, which is expressed by the following expression (12), is calculated based on the calculated position vector ($\vec{t}$) in the camera coordinate system, of the origin in the head coordinate system and the rotation matrix (R):

$$\vec{a} = (a_x, a_y, a_z) \quad (12).$$

17. An eyeball parameter estimating method according to claim 16, wherein, in the third step:

when image central coordinates are expressed by (v, w) and a focal distance is expressed by f, pupil central coordinates (lx, ly, lz) in the camera coordinate system are expressed by the following expressions (13) and (14):

$$l_x = \frac{l'x - v}{f} l_z = kx l_z; \text{ and} \quad (13)$$

$$l_y = \frac{l'y - w}{f} l_z = ky l_z; \quad (14)$$

a distance X between the origin (O") in the camera coordinate system and the eyeball center (O) is obtained by the following expression (15):

$$X = |\vec{X}| = |\vec{t} + \vec{a}| \quad (15);$$

the following expressions (16) and (17) are derived:

$$lx^2 + ly^2 + lz^2 = (X - r)^2; \text{ and} \quad (16)$$

$$lz = \frac{X - r}{\sqrt{1 + kx^2 + ky^2}} = \frac{K_1}{k_2}; \quad (17)$$

the pupil central coordinates in the camera coordinate system are set by the following expression (18) using the expressions (13), (14), and (17):

$$\begin{bmatrix} lx \\ ly \\ lz \end{bmatrix} = \frac{k_1}{k_2} \begin{bmatrix} kx \\ ky \\ 1 \end{bmatrix}; \text{ and} \quad (18)$$

a vector $\vec{E}$ pointing from the pupil center (i) to the eyeball center (O) in the camera coordinate system is obtained by the following expression (19):

$$\vec{E} = \frac{|\vec{O} - \vec{i}|}{|\vec{t} + \vec{a}|} (\vec{t} + \vec{a}) = \frac{r}{X} (\vec{t} + \vec{a}). \quad (19)$$

18. An eyeball parameter estimating method according to claim 17, wherein:
in the fourth step an evaluation function J is calculated by the following expression (20):

$$J = |X\vec{E} - Y\vec{X}| \tag{20}$$

where Y indicates an absolute value of a difference $\vec{Y}$ between a position vector $\vec{O}$ of the eyeball center (O) and a position vector $\vec{i}$ of the pupil center (i); and
in the fourth step, first eyeball parameters (r, θ) are estimated so as to minimize the evaluation function J expressed by the expression (20).

19. An eyeball parameter estimating method according to claim 18, wherein, in the fourth step:
partial differentiation of a variable (r') with respect to the eyeball radius (r) and partial differentiation of the eyeball central coordinates in the head coordinate system with respect to second eyeball parameters (r', θ) are calculated by the following expressions (21) to (27):

$$\frac{\partial r'}{\partial r} = \frac{r}{\sqrt{r^2 - L^2}}; \tag{21}$$

$$\frac{\partial O_x}{\partial r'} = R'_{00}\cos\theta + R'_{01}\sin\theta; \tag{22}$$

$$\frac{\partial O_y}{\partial r'} = R'_{10}\cos\theta + R'_{11}\sin\theta; \tag{23}$$

$$\frac{\partial O_z}{\partial r'} = R'_{20}\cos\theta + R'_{21}\sin\theta; \tag{24}$$

$$\frac{\partial O_x}{\partial \theta} = r'(-R'_{00}\sin\theta + R'_{01}\cos\theta); \tag{25}$$

$$\frac{\partial O_y}{\partial \theta} = r'(-R'_{10}\sin\theta + R'_{11}\cos\theta); \text{ and} \tag{26}$$

$$\frac{\partial O_z}{\partial \theta} = r'(-R'_{20}\sin\theta + R'_{21}\cos\theta); \tag{27}$$

partial differentiation of $|\vec{X}|^2$ with respect to the eyeball central position (O) is calculated by the following expressions (28) to (30):

$$\frac{\partial |\vec{X}|^2}{\partial O_x} = 2\{(t_x + a_x)R_{00} + (t_y + a_y)R_{01} + (t_z + a_z)R_{02}\} = 2A; \tag{28}$$

$$\frac{\partial |\vec{X}|^2}{\partial O_y} = 2\{(t_x + a_x)R_{01} + (t_y + a_y)R_{11} + (t_z + a_z)R_{21}\} = 2B; \tag{29}$$

and $$\frac{\partial |\vec{X}|^2}{\partial O_z} = 2\{(t_x + a_x)R_{02} + (t_y + a_y)R_{12} + (t_z + a_z)R_{22}\} = 2C; \tag{30}$$

partial differentiation of $|\vec{Y}|^2$ with respect to the eyeball central position (O) is calculated by the following expression (31):

$$\frac{\partial |\vec{Y}|^2}{\partial O_i} = 2(O_i - I_i)(i = x, y, z); \tag{31}$$

partial differentiation of $|\vec{E}|^2$ with respect to the eyeball central position (O) is calculated by the following expressions (32) to (34) using kx and ky in the expressions (13) and (14), $k_2$ in the expression (17), and A, B, and C in the expressions (28), (29), and (30) when $(\vec{Y})x$, $(\vec{Y})y$, and $(\vec{Y})z$ indicate x-, y-, and z-components of $\vec{Y}$, respectively:

$$\frac{\partial |\vec{E}|^2}{\partial O_x} = 2\left\{(t_x + a_x - I_x)\left(R_{00} - \frac{k_x A}{k_2 X} + \frac{k_x (\vec{Y})_x}{k_2 Y}\right)\right\} + \tag{32}$$

$$(t_y + a_x - I_x)\left(R_{10} - \frac{k_y A}{k_2 X} + \frac{k_y (\vec{Y})_x}{k_2 Y}\right) +$$

$$(t_z + a_z - I_z)\left(R_{20} - \frac{A}{k_2 X} + \frac{(\vec{Y})_x}{k_2 Y}\right);$$

$$\frac{\partial |\vec{E}|^2}{\partial O_y} = 2\left\{(t_x + a_x - I_x)\left(R_{01} - \frac{k_x B}{k_2 X} + \frac{k_x (\vec{Y})_y}{k_2 Y}\right)\right\} + \tag{33}$$

$$(t_y + a_y - I_y)\left(R_{11} - \frac{k_y B}{k_2 X} + \frac{k_y (\vec{Y})_y}{k_2 Y}\right) +$$

$$(t_z + a_z - I_z)\left(R_{21} - \frac{B}{k_2 X} + \frac{(\vec{Y})_y}{k_2 Y}\right); \text{ and}$$

$$\frac{\partial |\vec{E}|^2}{\partial O_z} = 2\left\{(t_x + a_x - I_x)\left(R_{02} - \frac{k_x C}{k_2 X} + \frac{k_x (\vec{Y})_z}{k_2 Y}\right)\right\} + \tag{34}$$

$$(t_y + a_y - I_y)\left(R_{12} - \frac{k_y C}{k_2 X} + \frac{k_y (\vec{Y})_z}{k_2 Y}\right) +$$

$$(t_z + a_z - I_z)\left(R_{22} - \frac{C}{k_2 X} + \frac{(\vec{Y})_z}{k_2 Y}\right);$$

partial differentiation of $\vec{E} \cdot \vec{X}$ with respect to the eyeball central position (O) is calculated by the following expressions (35) to (37) using kx and ky in the expressions (13) and (14), $k_2$ in the expression (17), and A, B, and C in the expressions (28), (29), and (30) when $M = 1/k_2 X$ and $P = 1/k_2 Y$:

$$\frac{\partial (\vec{E} \cdot \vec{X})}{\partial O_x} = [R_{00} - k_x\{MA - P(\vec{Y})_x\}](t_x + a_x) + \tag{35}$$

$$(t_x + a_x - I_x)R_{00} + [R_{10} - k_y\{MA - P(\vec{Y})_x\}](t_y + a_y) + (t_y + a_y - I_y)$$

$$R_{10} + [R_{20} - \{MA - P(\vec{Y})_x\}](t_z + a_z) + (t_z + a_z - I_z)R_{20};$$

$$\frac{\partial (\vec{E} \cdot \vec{X})}{\partial O_y} = [R_{01} - k_x\{MB - P(\vec{Y})_y\}](t_x + a_x) + \tag{36}$$

$$(t_x + a_x - I_x)R_{01} + [R_{11} - k_y\{MB - P(\vec{Y})y\}](t_y + a_y) +$$

$$(t_y + a_y - I_y)R_{11} + [R_{21} - \{MB - P(\vec{Y})_y\}](t_z + a_z) +$$

$$(t_z + a_z - I_z)R_{21}; \text{ and}$$

$$\frac{\partial (\vec{E} \cdot \vec{X})}{\partial O_z} = [R_{02} - k_x\{MC - P(\vec{Y})_z\}](t_x + a_x) + \tag{37}$$

$$(t_x + a_x - I_x)R_{02} + [R_{12} - k_y\{MC - P(\vec{Y})_z\}](t_y + a_y) +$$

$$(t_y + a_y - I_y)R_{12} + [R_{22} - \{MC - P(\vec{Y})_z\}](t_z + a_z) +$$

$$(t_z + a_z - I_z)R_{22};$$

partial differentiation of the evaluation function (J) with respect to the eyeball central position (O) is calculated by the following expression (38) based on results obtained by the partial differentiations calculated above:

$$\frac{\partial J}{\partial O_i} = \frac{\partial |\vec{X}|^2}{\partial O_i}|\vec{E}|^2 + |\vec{X}|^2\frac{\partial |\vec{E}|^2}{\partial O_i} - \frac{|\vec{Y}|\partial |\vec{X}|^2}{|\vec{X}|\partial O_i}(\vec{E} \cdot \vec{X}) - \frac{|\vec{X}|\partial |\vec{Y}|^2}{|\vec{Y}|\partial O_i}(\vec{E} \cdot \vec{X}) - \tag{38}$$

-continued $$2|\vec{X}||\vec{Y}|\frac{\partial(\vec{E}\cdot\vec{X})}{\partial O_i}+|\vec{X}|^2\frac{\partial|\vec{Y}|^2}{\partial O_i}+|\vec{Y}|^2\frac{\partial|\vec{X}|^2}{\partial O_i}(i=x,y,z);$$

partial differentiation of the evaluation function (J) with respect to the first eyeball parameters (r, θ) is calculated by the expressions (22) to (27), the expression (38), and the following expressions (39) and (40):

$$\frac{\partial J}{\partial r}=\frac{\partial r'}{\partial r}\left(\frac{\partial O_x}{\partial r'}\frac{\partial J}{\partial O_x}+\frac{\partial O_y}{\partial r'}\frac{\partial J}{\partial O_y}+\frac{\partial O_z}{\partial r'}\frac{\partial J}{\partial O_z}\right); \text{ and} \quad (39)$$

$$\frac{\partial J}{\partial \theta}=\frac{\partial O_x}{\partial \theta}\frac{\partial J}{\partial O_x}+\frac{\partial O_y}{\partial \theta}\frac{\partial J}{\partial O_y}+\frac{\partial O_z}{\partial \theta}\frac{\partial J}{\partial O_z}; \text{ and} \quad (40)$$

the evaluation function (J) is compared with the threshold (Th),
when the evaluation function (J) becomes smaller than the threshold (Th), eyeball parameter estimation processing is completed, and
when the evaluation function (J) is larger than the threshold (Th), the eyeball parameter estimation processing is continued.

20. An eyeball parameter estimating method according to claim 19, wherein, in the fourth step, the first eyeball parameters (r, θ) are updated by the following expressions (41) and (42) using the expressions (39) and (40):

$$r \leftarrow r + \rho\frac{\partial J}{\partial r}; \text{ and} \quad (41)$$

$$\theta \leftarrow \theta + \rho\frac{\partial J}{\partial \theta}. \quad (42)$$

21. A recording medium storing a program for causing a computer to function as:
a head posture estimating unit that estimates, from a face image of a person photographed by a camera, position data ($\vec{t}$) corresponding to three degrees of freedom (x-, y-, z-axes) in a camera coordinate system, of an origin (O') in a head coordinate system and rotation angle data (R) corresponding to three degrees of freedom (x-, y-, z-axes) of a coordinate axis of the head coordinate system relative to a coordinate axis of the camera coordinate system, as head posture data ($\vec{t}$, R) in the camera coordinate system;
a head coordinate system eyeball central position candidate setting unit that sets candidates of eyeball central position data ($\vec{a}'$) in the head coordinate system based on coordinates of two feature points on an eyeball, which are preliminarily set in the head coordinate system;
a camera coordinate system eyeball central position calculating unit that calculates an eyeball central position ($\vec{a}$) in the camera coordinate system based on the head posture data ($\vec{t}$, R), the eyeball central position candidate data ($\vec{a}'$), and pupil central position data detected from the face image; and
an eyeball parameter estimating unit that estimates an eyeball central position (O) and an eyeball radius (r) in the head coordinate system based on the eyeball central position ($\vec{a}$) in the camera coordinate system so as to minimize deviations of position data of a point of gaze (O"), a pupil center (i), and an eyeball center (O) from a straight line joining original positions of the three piece of position data.

22. A recording medium according to claim 21, wherein the two feature points on the eyeball which are used include an inner corner and an outer corner of an eye.

23. A recording medium according to claim 22, wherein the point of gaze which is used includes a lens center (O") of the camera for obtaining the face image.

* * * * *